(12) United States Patent
Suzuki et al.

(10) Patent No.: US 8,049,051 B2
(45) Date of Patent: Nov. 1, 2011

(54) PROCESS FOR PRODUCTION OF AROMATIC HYDROCARBONS

(75) Inventors: Yushi Suzuki, Yokohama (JP); Tsuyoshi Asano, Yokohama (JP)

(73) Assignees: Nippon Oil Corporation, Kanagawa (JP); Chiyoda Corporation, Kanagawa (JP)

( * ) Notice: Subject to any disclaimer, the term of this patent is extended or adjusted under 35 U.S.C. 154(b) by 492 days.

(21) Appl. No.: 12/376,656

(22) PCT Filed: Aug. 2, 2007

(86) PCT No.: PCT/JP2007/065564
§ 371 (c)(1),
(2), (4) Date: Feb. 6, 2009

(87) PCT Pub. No.: WO2008/018522
PCT Pub. Date: Feb. 14, 2008

(65) Prior Publication Data
US 2009/0177020 A1   Jul. 9, 2009

(30) Foreign Application Priority Data

Aug. 7, 2006  (JP) ................. 2006-214842
Aug. 7, 2006  (JP) ................. 2006-214843

(51) Int. Cl.
*C07C 2/54* (2006.01)
(52) U.S. Cl. ....................... 585/412; 585/418
(58) Field of Classification Search .......... 585/412, 585/418
See application file for complete search history.

(56) References Cited

U.S. PATENT DOCUMENTS

| 3,992,465 | A | | 11/1976 | Juguin et al. |
| 4,861,934 | A | | 8/1989 | Suzuki et al. |
| 4,879,424 | A | * | 11/1989 | Harandi .................. 585/322 |
| 5,073,673 | A | | 12/1991 | Hirabayashi et al. |

FOREIGN PATENT DOCUMENTS

| EP | 0107875 A2 | 5/1984 |
| EP | 0913452 A1 | 5/1999 |
| JP | 59098020 A | 6/1984 |
| JP | 60501357 A | 8/1985 |
| JP | 62254847 A | 11/1987 |
| JP | 03072596 A | 3/1991 |
| JP | 11172261 A | 6/1999 |
| WO | 84/03879 A1 | 10/1984 |

OTHER PUBLICATIONS

Hiroshi Ohashi, "Keishitsu Tankasuiso no Hokozokuka Gijutsu Saishin no Shinpo", Idemitsu Technical Report, vol. 39, No. 3, pp. 223-228, 1996.

* cited by examiner

*Primary Examiner* — Thuan Dinh Dang
(74) *Attorney, Agent, or Firm* — Panitch Schwarze Belisario & Nadell LLP

(57) ABSTRACT

The present invention provides a process for producing aromatic hydrocarbons at a sufficiently high yield, from a light hydrocarbon containing mainly hydrocarbons having 7 or fewer carbon atoms. The process of the present invention comprises bringing a feedstock containing mainly light hydrocarbons having 2 to 7 carbon atoms into contact with a catalyst composition comprising at least a gallium-containing crystalline aluminosilicate wherein a reaction step for converting the feedstock to aromatic hydrocarbons comprises at least two or more reaction layers formed of the catalyst composition, arranged in series and heating means arranged either between or in the reaction layers, the amount of the catalyst in the first stage reaction layer is 30 percent by volume or less of the total catalyst volume, and/or the yield of the aromatics in the product outflowing from the first reaction layer is from 0.5 to 30 percent by mass.

10 Claims, 1 Drawing Sheet ions No. WO 2008/018522 A1, and the
PROCESS FOR PRODUCTION OF AROMATIC HYDROCARBONS

CROSS-REFERENCE TO RELATED APPLICATION

This application is a Section 371 of International Application No. PCT/JP2007/065564, filed Aug. 2, 2007, which was published in the Japanese language on Feb. 14, 2008, under International Publication No. WO 2008/018522 A1, and the disclosure of which is incorporated herein by reference.

FIELD OF THE INVENTION

The present invention relates to a process for producing aromatic hydrocarbons from a light hydrocarbon containing mainly hydrocarbons having 2 to 7 carbon atoms, used as the feedstock.

BACKGROUND OF THE INVENTION

Conventionally, catalytic reforming of straight run naphtha with a platinum/alumina catalyst has been employed widely for commercial purposes in order to produce gasoline with a higher octane number or aromatic hydrocarbons. The feedstock naphtha for the catalytic reforming is a fraction with a boiling point of 70 to 180° C. when an automobile gasoline is intended to be produced and a fraction with a boiling point of 60 to 150° C. when aromatic hydrocarbons such as xylene, that is BTX, are intended to be produced. However, it has been difficult to produce high octane number gasolines and aromatic hydrocarbons from a feedstock light hydrocarbon containing mainly hydrocarbons having 7 or fewer carbon atoms at a high yield with the conventional catalytic reforming processes because the conversion rate of the feedstock hydrocarbon to aromatics decreases with a decrease in the carbon atom number of the feedstock hydrocarbon, resulting in a decrease in the octane number of the resulting product. Therefore, the usage of the light hydrocarbon is limited to petrochemical raw materials and raw materials for the production of city gas.

Various processes for producing aromatic hydrocarbons from a light hydrocarbon are known in which a light hydrocarbon is brought into contact with a gallium-containing crystalline silicate catalyst such as a crystalline gallosilicate (Japanese Patent Application Laid-Open Publication No. 59-98020), a crystalline galloaluminosilicate (Japanese Patent Application Laid-Open Publication No. 60-501357), or a hydrogen-type crystalline aluminogallosilicate of MFI structure (Japanese Patent Application Laid-Open Publication No. 62-254847).

However, these catalytic reforming processes are large endothermal reactions and thus fail to proceed with the reaction because the reaction temperature decreases unless the reaction layers are efficiently supplied with heat, resulting in a problem that aromatic hydrocarbons can not be produced at a high yield.

For catalytic reforming of a hydrocarbon fraction within the gasoline boiling point range with a conventional platinum/alumina catalyst in the presence of hydrogen, a process is known in which a plurality of catalyst reaction layers are arranged in series and heating means are arranged therebetween (U.S. Pat. No. 3,992,465). However, this catalytic reforming of a gasoline fraction is different in the composition of the feedstock and catalyst system from the above-described processes for the production of aromatics from a light hydrocarbon. Further, this patent document does not disclose the volume distribution of the plurality of reaction layers or the composition of the product outflowing from each of the reaction layers or suggest that the yield of the aromatics in the converted reaction product is significantly increased depending on the selection of the distribution or composition. Japanese Patent Application Laid-Open Publication No. 11-172261 discloses a catalytic reforming process for increasing BTX by providing two reforming zones. However, this process is complicated because different types of catalysts are used in those reforming zones.

As described above, for the production of aromatic hydrocarbons from a light hydrocarbon containing mainly hydrocarbons having 7 or fewer carbon atoms, a process wherein aromatic hydrocarbons are produced at a high yield has not been known yet.

DISCLOSURE OF THE INVENTION

The present invention has an object to provide a process for producing aromatic hydrocarbons at a high yield from a light hydrocarbon containing mainly hydrocarbons having 7 or fewer carbon atoms.

As the result of the extensive study and research to achieve the object, the present invention was accomplished on the basis of the finding that when the amount of a catalyst in a first stage reaction layer in a conversion reaction step is adjusted to 30 percent by volume or less of the total catalyst volume and/or the yield of aromatics in the effluent from the first reaction layer in the conversion reaction step is adjusted to 0.5 to 30 percent by mass, the yield of the aromatic hydrocarbons in the effluent from the whole conversion reaction step was able to be increased significantly compared with the conventional processes.

That is, the present invention relates to a process for producing aromatic hydrocarbons, comprising bringing a feedstock containing mainly a light hydrocarbon having 2 to 7 carbon atoms into contact with a catalyst composition comprising at least a gallium-containing crystalline aluminosilicate, wherein a reaction step for converting the feedstock to aromatic hydrocarbons comprises at least two or more reaction layers formed of the catalyst composition, arranged in series and heating means arranged either between or in the reaction layers, and the amount of the catalyst in a first stage reaction layer is 30 percent by volume or less of the total catalyst volume.

The present invention also relates to a process for producing aromatic hydrocarbons comprising bringing a feedstock containing mainly a light hydrocarbon having 2 to 7 carbon atoms into contact with a catalyst composition comprising at least a gallium-containing crystalline aluminosilicate, wherein a reaction step for converting the feedstock to aromatic hydrocarbons comprises at least two or more reaction layers formed of the catalyst composition, arranged in series and heating means arranged either between or in the reaction layers, and the yield of the aromatics in the effluent from a first stage reaction layer is from 0.5 to 30 percent by mass.

The present invention also relates to a process for producing aromatic hydrocarbons comprising bringing a feedstock containing mainly light hydrocarbons having 2 to 7 carbon atoms into contact with a catalyst composition comprising at least a gallium-containing crystalline aluminosilicate wherein a reaction step for converting the feedstock to aromatic hydrocarbons comprises at least two or more reaction layers formed of the catalyst composition, arranged in series and heating means arranged either between or in the reaction layers, the amount of the catalyst in a first stage reaction layer is 30 percent by volume or less of the total catalyst volume, and the yield of the aromatics in the product outflowing from the first stage reaction layer is from 0.5 to 30 percent by mass.

BEST MODE FOR CARRYING OUT THE INVENTION

Figure 1:
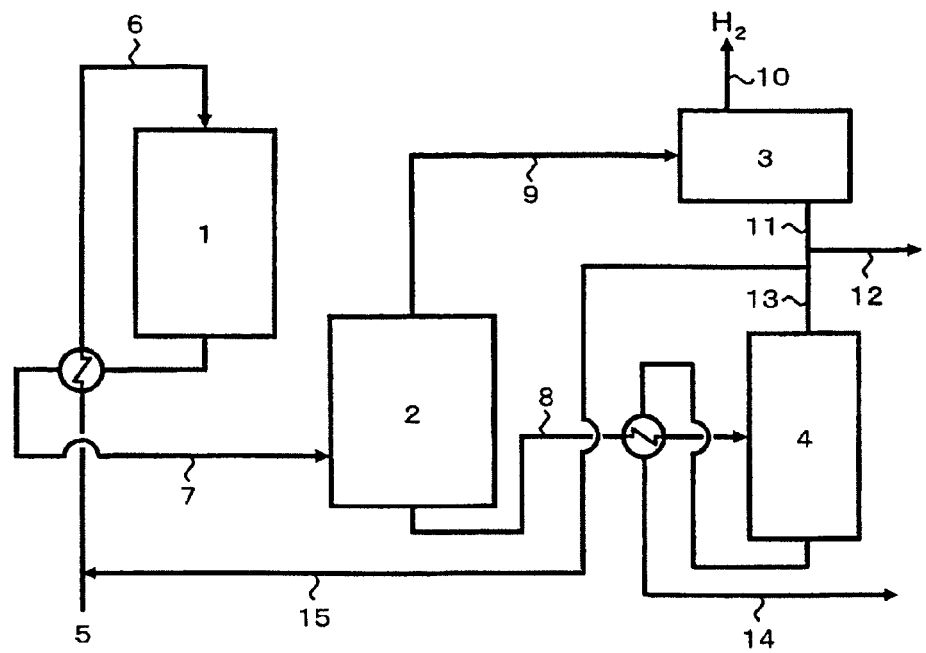
FIG. 1 is a flow chart illustrating exemplarily the operation of the process of the present invention.

The present invention will be described in more detail below.

The light hydrocarbon used as the feedstock in the present invention contains mainly a hydrocarbon having 2 to 7 carbon atoms. There is no particular restriction on the content of the hydrocarbon having 2 to 7 carbon atoms. However, the content is preferably 20 percent by mass or more, more preferably 40 percent by mass or more, particularly preferably 60 to 100 percent by mass.

There is no particular restriction on the hydrocarbon having 2 to 7 carbon atoms which may, therefore, be straight-chain, branched or cyclic and paraffin, olefin or mixtures thereof. Specific examples of the hydrocarbon include those having 2 to 7 carbon atoms, such as straight-chain aliphatic saturated hydrocarbons (ethane, propane, butane, pentane, hexane and heptane), branched aliphatic saturated hydrocarbons (isobutane, 2-methylbutane, 2,2-dimethylbutane, 2-methylpentane, 3-methylpentane, 2,3-dimethylbutane, 2-methylhexane, 3-methylhexane, 2,2-dimethylpentane, 2,3-dimethylpentane, 2,4-dimethylpentane, and 2,2,3-trimethylbutane), cyclic aliphatic saturated hydrocarbons (cyclopropane, cyclobutane, cyclopentane, 1-methylcyclopentane, 1,1-dimethylcyclopentane, 1,2-dimethylcyclopentane, 1,3-dimethylcyclopentane, cyclohexane, and 1-methylcyclohexane), straight-chain aliphatic unsaturated hydrocarbons (ethylene, propylene, butene, pentene, hexene, and heptene), branched aliphatic unsaturated hydrocarbons (isobutene, 2-methylbutene, 2-methylpentene, 3-methylpentene, 2-methylhexene, and 3-methylhexene), cyclic aliphatic unsaturated hydrocarbons (cyclopentene, methylcyclopentene, cyclohexene, and methylcyclohexene), liquefied petroleum gas containing mainly propane or butane, light fractions (light naphtha) with a boiling point of 100° C. or lower in a naphtha fraction containing mainly paraffin having 5 to 7 carbon atoms, C4 fractions produced in a fluid catalytic cracking (FCC) unit, and raffinate produced through an ethylene cracker.

The catalyst composition used in the present invention contains at least a gallium-containing crystalline aluminosilicate, the content of which is not particularly restricted. However, the content is preferably 50 percent by mass or more, more preferably 70 percent by mass or more.

Gallium-containing crystalline aluminosilicates used in the present invention may be those where gallium is incorporated in the lattice skeleton of a crystalline aluminosilicate (crystalline aluminogallosilicates), those where gallium is supported on a crystalline aluminosilicate (Ga-supporting crystalline aluminosilicates) or those containing both of them, and are preferably those containing at least a crystalline aluminogallosilicate.

The Ga-supporting crystalline aluminosilicate is produced by loading gallium on a crystalline aluminosilicate by a conventional technique such as ion-exchange method or impregnation method. The gallium source used thereupon may be a gallium salt such as gallium nitrate or gallium chloride or gallium oxide.

The crystalline aluminogallosilicate has a structure where $SiO_4$, $AlO_4$ and $GaO_4$ structures form a tetrahedral coordination in the skeleton and can be produced by hydrothermal gel-crystallization, incorporating gallium in the lattice skeleton of a crystalline aluminosilicate, or incorporating aluminum in the lattice skeleton of a crystalline gallosilicate.

The gel-crystallization method is an easy and excellent method because aluminum and gallium in the intended amounts are included at the same time to prepare a crystalline aluminogallosilicate. When the crystalline aluminogallosilicate is synthesized by gel-crystallization, it can be produced by retaining a slurry-like aqueous mixture containing an alumina source, a silica source, and a gallia source as the essential components under hydrothermal synthesis conditions. For example, the alumina source may be an aluminum salt such as aluminum sulfate or aluminum nitrate, an aluminate such as sodium aluminate, or alumina-gel. The silica source may be a silicate such as sodium silicate or potassium silicate, colloidal silica, silica powder, dissolved silica, or water glass. The gallia source may be a gallium salt such as gallium nitrate or gallium chloride, or gallium oxide. Alternatively, the alumina and gallia sources may be a solution or oxide containing aluminum and gallium produced through processes of extraction and refining of ore deposits such as bauxite ore deposits and zinc ore deposits. Organic additives and alkali metal and alkaline earth metal sources may be used so as to expedite the crystallization of the intended crystalline aluminogallosilicate and improve the purity thereof. Examples of the organic additives include quaternary ammonium salts such as tetrapropylammonium salt, tetrabutylammonium salt and tripropylmethylammonium salt, amines such as propylamine, butylamine, aniline, dipropylamine, dibutylamine and morpholine, aminoalcohols such as ethanol amine, diglycol amine, and diethanol amine, alcohols such as ethanol, propyl alcohol, ethylene glycol, and pinacol, organic acids, ethers, ketones, amino acids, esters, thioalcohols, and thioethers. Further alternatively, a compound may be used which produces the aforesaid organic additives under hydrothermal synthesis conditions. Examples of the alkali metal sources and alkaline earth metal sources include hydroxides, halides, sulfates, nitrates and carbonates of alkali metals such as sodium and potassium and alkaline earth metals such as magnesium and calcium. In addition to these compounds, the raw materials of the catalyst may contain mineral acids such as sulfuric acid and nitric acid as pH adjusters. An aqueous raw material mixture containing one or more type of compounds which will be the raw materials of the above-described components is crystallized by retaining at a temperature of 140° C. or higher, preferably 150 to 250° C. under self-pressure for one hour to 7 days, preferably 2 hours to 5 days, while being stirred. The use of these crystallization conditions renders it possible to produce efficiently a crystalline aluminogallosilicate with excellent reaction activity. Although a crystalline aluminogallosilicate with excellent reaction activity can be produced even at a crystallization temperature of lower than 140° C. by prolonging the crystallization time, it is not economical. The zeolite crystal phase of this crystalline aluminogallosilicate is in a metastable phase. It is thus not preferable to place the crystalline aluminogallosilicate under the hydrothermal conditions for a long time because other phases that are not intended may be produced and mixed in the crystalline aluminogallosilicate if the crystal once produced is placed under the hydrothermal conditions for a long time.

The gallium-containing crystalline aluminosilicate used in the present invention preferably contains 80 percent by mass or more of particles having a diameter of 0.05 to 20 μm, preferably 0.1 to 10 μm, more preferably 0.5 to 5 μm, more preferably 1 to 3 μm. When the size of reactant molecules and the size of the zeolite micro pores are substantially the same, the diffusion rate of the molecules becomes slow in the zeolite micro pores. Therefore, when the particle diameter is in excess of 20 μm, the reactant molecules can not approach easily to the active sites in the deep portion of the micro pores, and thus the active sites can not be used effectively during the reaction. Further, due to coke deposition on the outer surfaces of the gallium-containing crystalline aluminosilicate, the entrances of the micro pores are blocked with the coke, and thus the deep portions of the pores are not utilized effectively, resulting in a decrease in activity and selectivity.

When the crystalline aluminogallosilicate or crystalline aluminosilicate is produced by hydrothermal synthesis, examples of factors affecting the size of the resulting particles include the type of the silica source, the amount of the organic additives such as a quaternary ammonium salt, the amount and type of the inorganic salt used as a mineralizer, the amount of the base in the gel, the pH of the gel, and the temperature and stirring speed upon crystallization. Adjusting these conditions properly makes it possible to produce a gallium-containing crystalline aluminosilicate with the above-described particle diameter range.

The reaction activity of a gallium-containing crystalline aluminosilicate is affected depending on the composition thereof. In order to obtain a higher reaction activity, the gallium-containing crystalline aluminosilicate contains an aluminum element in an amount of preferably 0.1 to 2.5 percent by mass, more preferably 0.1 to 2.0 percent by mass and a gallium element in an amount of preferably 0.1 to 5.0 percent by mass, more preferably 0.1 to 3.0 percent by mass. The molar ratio of $SiO_2/(Al_2O_3+Ga_2O_3)$ is in the range of preferably 17 to 600, more preferably 19 to 250, more preferably 25 to 200 with the objective of retaining the reaction activity at a higher level for a long time. The molar ratio of $SiO_2/Al_2O_3$ is in the range of preferably 32 to 870, more preferably 35 to 300 while the molar ratio of $SiO_2/Ga_2O_3$ is in the range of preferably 36 to 2000, more preferably 40 to 500.

The composition of the gallium-containing crystalline aluminosilicate is preferably represented by the molar ratio of the oxides resulting from calcination at a temperature of 500° C. or higher as represented by the following formula:

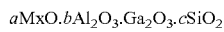

$aMxO.bAl_2O_3.Ga_2O_3.cSiO_2$ wherein M is an alkali metal or alkaline earth metal, x is 2 when M is an alkali metal and 1 when M is an alkaline earth metal, a to c are the following numerical values:

a: an integer of (b+1)±3.0, preferably (b+1)±2.0;
b: 0.04 to 62.5, preferably 0.1 to 14.0; and
c: 36 to 2000, preferably 40 to 500.

MASNMR (Magic Angle Spinning Nuclear Magnetic Resonance) analysis can provide directly or indirectly useful information regarding elements present in the crystalline structure of a crystalline silicate and composition thereof. For example, for a crystalline aluminosilicate, $^{27}$Al-NMR can provide the information regarding Al of the tetrahedral coordination in the anionic skeleton structure. Further, the information regarding four tetrahedrons ($TO_4$: T=Al, Ga, Si) adjacent to ($SiO_4$) in the structure can be obtained by $^{29}$Si-NMR. For the crystalline aluminogallosilicate described in the specification, the presence of Al and Ga in the tetrahedral coordination in the skeleton structure were indicated by $^{27}$Al-NMR and $^{71}$Ga-NMR, and the molar ratio of $SiO_2/(Al_2O_3+Ga_2O_3)$ in the crystalline structure was calculated from the information obtained by $^{29}$Si-NMR analysis. The resulting calculated value was well-consistent with the value obtained as the result of the elemental analysis of the crystalline aluminogallosilicate.

One of the chemical characteristics of the crystalline aluminogallosilicate is acid property. Generally, the amount of acid can be determined by temperature-programmed desorption or adsorption heat measurement using a basic substance such as ammonia or pyridine. For the crystalline aluminogallosilicate, the amount of acid corresponding to the amounts of aluminum and gallium was measured, and this indicates that aluminum and gallium are present in the anionic skeleton structure in the zeolite crystal structure.

Crystalline aluminogallosilicates particularly useful for the present invention are those of MFI type and/or MEL type crystal structures. The crystalline aluminogallosilicates of MFI and MEL types belong to the known zeolite structure types reported by "The Structure Commission of the International Zeolite Association (Atlas of Zeolite Structure Types, W. M. Meiyer and D. H. Olson (1978) distributed by Polycrystal Book Service, Pittsburgh, Pa., USA).

Alternatively, if desired, the gallium-containing crystalline aluminosilicate may be subjected to various activation treatments for zeolites. Therefore, the gallium-containing crystalline aluminosilicate referred herein include not only those produced by the above-described hydrothermal synthesis but also those further subjected to modification treatment or activation treatment. For example, a crystalline aluminogallosilicate is ion-exchanged in an aqueous solution containing an ammonium salt such as ammonium chloride, ammonium fluoride, ammonium nitrate or ammonium hydroxide so as to be of ammonium type and then ion-exchanged in an aqueous solution containing metal ions other than those of alkali metals or alkaline earth metals or impregnated with the aqueous solution to incorporate desired metals other than alkali metals or alkaline earth metals. Alternatively, the gallium-containing crystalline aluminosilicate of ammonium type may be activated so as to be of acid type by heating at a temperature of 200 to 800° C., preferably 350 to 700° C. under an air, nitrogen or hydrogen atmosphere for 3 to 24 hours to remove the ammonia. Further alternatively, the resulting acid type catalyst may be treated with hydrogen or a mixed gas of hydrogen and nitrogen under the foregoing conditions. Further, the acid type catalyst may be subjected to an ammonia modification where it is brought into contact with ammonia under dry conditions. Generally, the catalyst composition used in the present invention is preferably subjected to the foregoing activation treatments before being brought into contact with the feedstock hydrocarbon.

In addition to the above-described gallium-containing crystalline aluminosilicate, the catalyst composition of the present invention may contain a binder. The binder refers to a substance for enhancing the mechanical properties (strength, wear resistance, formability) of the catalyst. Examples of such a substance include inorganic oxides such as alumina, alumina-boria, silica and silica-alumina. There is no particular restriction on the content of the substance. However, the substance is added to be present in an amount of 50 percent by mass or less, preferably 30 percent by mass or less in the catalyst composition. Alternatively, addition of phosphorus in these inorganic binders can further enhance the mechanical strength of a shaped product. A mixture of the gallium-containing aluminosilicate and the binder can be formed into various shaped products such as particles, spheres, plates, and pellets by a method such as extrusion, spray drying, tablet compression, rolling granulation or oil granulation. Upon shaping, it is desirous to use a lubricant of an organic compound in order to improve the formability.

Generally, shaping of a mixture of the gallium-containing crystalline aluminosilicate and the binder may be carried out before or after the aluminosilicate is ion-exchanged with ammonium ion or the like.

Alternatively, a metal component may be loaded as an auxiliary component on the catalyst composition of the present invention. The auxiliary metal component may be supported on the gallium-containing crystalline aluminosilicate and/or the binder for shaping. Alternatively, the auxiliary metal component may be added as the third component when the gallium-containing crystalline aluminosilicate is shaped with the binder. Examples of the auxiliary metal component include metals with dehydrogenation capability and metals that are effective in suppressing carbon deposition. Specific examples of the auxiliary metals that can improve catalyst activity include magnesium, calcium, strontium, barium, lanthanum, cerium, praseodymium, neodymium, samarium, europium, gadolinium, terbium, dysprosium, holmium, erbium, thulium, ytterbium, lutetium, titanium, vanadium, chromium, molybdenum, tungsten, manganese, rhenium, iron, ruthenium, cobalt, rhodium, iridium, nickel, palladium, platinum, copper, silver, zinc, aluminum, indium, germanium, tin, lead, phosphorus, antimony, bismuth, and selenium. These metals may be used alone or in combination. The amount of the metal to be supported is from 0.1 to 10 percent by mass in terms of metal. The metal may be loaded with a conventional technique such as ion-exchanging, impregnation or physical mixing. Alternatively, upon synthesis of the crystalline aluminogallosilicate or crystalline aluminosilicate, the metal components may be added as auxiliary components to be contained therein. One or more metals may be loaded as auxiliary metal components which are effective in suppressing coke deposition upon reaction. The metals are selected from the group consisting of magnesium, calcium, lanthanum, cerium, praseodymium, neodymium, samarium, europium, gadolinium, terbium, dysprosium, holmium, erbium, thulium, ytterbium, lutetium, ruthenium, and iridium. The amount of the metals to be supported is from 0.01 to 5 percent by mass.

Description will be given of each step of the process of the present invention.

(a) Conversion Reaction Step

For the conversion reaction step, at least n (n is the number of the layers and thus an integer of 2 or greater) reaction layers for retaining the above-described catalyst composition are arranged in series, and further heating means such as heating furnaces for heating effluent from the previous layer are arranged between and/or in the layers. Hereinafter, the reaction layers arranged in series are referred to as "first stage reaction layer", "second stage reaction layer" and so on from the upstream side. In this conversion reaction step, a mixture of a feedstock light hydrocarbon and recycling gas described below is allowed to pass through the reaction layers thereby converting the mixture to aromatic hydrocarbons.

The temperature at the entrances of the reaction layers is usually in the range of preferably 350 to 650° C. When the feedstock light hydrocarbon contains mainly n-paraffin, iso-paraffin or olefin, the temperature is preferably in the range of preferably 450 to 650° C., in the range of preferably 400 to 600° C., or in the range of preferably 350 to 550° C., respectively.

The hydrogen partial pressure is preferably 490 kPa (5 kgf/cm$^2$) or lower. The gas hourly space velocity of the feedstock is preferably from 100 to 2000 hr$^{-1}$.

The n reaction layers arranged in series in this conversion reaction step are arranged so that the amount of the catalyst in the first stage reaction layer is 30 percent by volume or less, preferably 1 to 30 percent by volume, more preferably 2 to 30 percent by volume, more preferably 2 to 28 percent by volume of the total catalyst volume. When the number n of the reaction layers in series is 3 or greater, the catalyst amount in the first stage reaction layer is preferably 60/n percent by volume or less of the total catalyst amount. As the result, the final yield of aromatic hydrocarbons is increased.

In the present invention, among the two or more reaction layers in series in the conversion reaction step, the aromatic yield in the effluent from the first stage reaction layer is preferably from 0.5 to 30 percent by mass, preferably from 2 to 30 percent by mass, more preferably 2 to 28 percent by mass. Particularly preferably, the number of the reaction layers is 3 or greater and the aromatic yield in the effluent from the first stage reaction layer is preferably from 2 to 25 percent by mass. As the result, the final aromatic yield is significantly increased.

There is no particular restriction on the method of adjusting the aromatic yield in the effluent from the first stage reaction layer. For example, adjusting the temperature at the entrance of the reaction layer and/or the filling ratio of the catalyst in each reaction layer may be employed.

In the present invention, particularly preferably the catalyst amount in the first stage reaction layer is 30 percent by volume or less of the total catalyst amount, and the aromatic yield in the effluent from the first stage reaction layer is from 0.5 to 30 percent by mass.

There is no particular restriction on the number n of the reaction layers as long as it is two or greater. However, too many reaction layers do not give significant changes and thus are not economical. Therefore, the number n is preferably 2 or greater and 8 or fewer, more preferably 3 or greater and 6 or fewer.

The conversion reaction step may be operated at a constant temperature at the entrance of the reaction layer or may be operated, elevating the temperature continuously or stepwise to obtain a given aromatic yield. When the aromatic yield falls below the given range or the temperature at the entrance of the reaction layer exceeds the given range, it is preferable to switch the catalyst reaction tower to that containing a new catalyst or the regenerated catalyst to continue the reaction. Regeneration of the catalyst may be carried out by heating the catalyst at a temperature of 200 to 800° C., preferably 350 to 700° C. in a flowing current of air, nitrogen, hydrogen or a mixed gas of nitrogen/hydrogen. The process of the present invention is preferably carried out using two lines of fixed bed reactors each containing the reaction layer retaining the above-described catalyst composition. In this case, the reactor in each line consists of a plurality of reaction layers arranged in series. While the feedstock light hydrocarbon is introduced to the reactor in one of the lines to proceed with the reaction, the catalyst in the reactor in the other line is regenerated. The reaction/regeneration is carried out alternately in the reactors in these two lines at an interval of one to 10 days thereby rendering it possible to operate the reactors continuously, for example, for one year. Alternatively, the whole or part of the reactor in the line in use for the reaction may be switched to the reactor in the other line to proceed with the reaction in a continuous manner like cyclic operation. Every one cycle of the reaction for 1 to 10 days, the reaction temperature is increased by 5 to 20° C. continuously or stepwise to retain the aromatic yield in the effluent from the final reaction layer in the predetermined range of 40 to 75 percent by mass.

The aromatic yield is represented by the following formula (Indicated by R in formula (1)):

$$R = A/B \times 100(\%) \quad (1)$$

A: the weight of the total aromatic hydrocarbon in the converted reaction product;

B: the weight of the aliphatic hydrocarbons having 2 to 7 carbon atoms, excluding ethane in the feedstock.

When an aliphatic hydrocarbon is converted to an aromatic hydrocarbon, a reaction accompanying dehydrogenation proceeds. Therefore, a partial pressure enabling the reaction can be obtained under the reaction conditions even though hydrogen is not added. Although intentional addition of hydrogen gives advantages that deposition of coke can be prevented and the frequency of catalyst regeneration can be lessened, it is not always advantageous because the aromatic yield is drastically decreased as the hydrogen partial pressure increases. Therefore, the hydrogen partial pressure is preferably held to 490 kPa (5 kgf/cm$^2$) or lower.

In the conversion reaction step in the process of the present invention, a light gas is preferably present, which gas contains methane and/or ethane to be circulated as a recycle gas generated from the subsequent separation step. The conversion reaction carried out in the presence of the light gas containing methane and/or ethane can suppress coke deposition on the catalyst and retain the aromatic yield at a higher level for a long time. The amount of the total light gas (recycle gas) to be circulated to the reaction system is from 0.1 to 10 part by weight, preferably from 0.5 to 3 part by weight per part by weight of the feedstock hydrocarbon to be supplied.

(b) Step of Gas-Liquid Separation of Effluent from Reaction Layers

This step is a step where the effluent from the reaction layers, produced through the above-described conversion reaction step is introduced into a gas-liquid separation zone where one or more gas-liquid separators are arranged and subjected to gas-liquid separation under relatively high pressure thereby separating a liquid component (hereinafter referred to as "high pressure separated liquid") containing mainly aromatic hydrocarbons and a light gas (hereinafter referred to as "high pressure separated gas") containing hydrogen, methane, ethane, propane and butane. The separation is carried out under conditions where the temperature is usually from 10 to 50° C., preferably from 20 to 40° C. and the pressure is usually from 5 to 80 atmosphere, preferably from 10 to 30 atmosphere. The effluent from the reaction layer is cooled by allowing it to indirectly exchange heat with the feedstock hydrocarbon the temperature of which is low before being introduced in the gas-liquid separation step, and if necessary, a part of the light gas may be separated in order to reduce the load in the gas-liquid separation step and a step where hydrogen is separated from the light gas.

(c) Step of Separation of Hydrogen Form Separated Gas

This step is a step where hydrogen is selectively separated from the high-pressure separated gas separated in the gas-liquid separation step to obtain the above-mentioned recycle gas containing methane and/or ethane. The method of separating hydrogen in this step may be carried out using a conventional method such as membrane separation or cryogenic separation. The use of membrane separation is preferable in view of selective hydrogen separation efficiency. However, when cryogenic separation is used to utilize the off gas generated therethrough as a recycle gas, it has an advantage that the unreacted propane can be reacted at the maximum compared with the utilization of the off gas obtained through membrane separation and thus the aromatic yield can be increased by 1 to 3 percent by mass. Which separation method is employed is determined in economical view. A membrane separation device is commercially available, in which polyimide, polysulfone or a blend membrane of polysulfone and polydimethylsiloxane is used as the separation membrane. A part of the recycle gas produced through this step is discharged to the outside of the system to retain the total circulating gas amount within a constant range. In order to recover hydrogen of high purity, a recovering system such as a membrane separation device or PSA (Pressure Swing Adsorption device) is preferably arranged in the subsequent stage of the membrane separation device. The device in the subsequent stage is selected in economical view.

(d) Step of Separating Aromatic Hydrocarbon from Separated Liquid

This step is a step where an aromatic hydrocarbon and a low boiling point hydrocarbon gas are separated from the high pressure separated liquid produced through the gas-liquid separation, and a stabilizer (distillation column) is used. The low boiling point hydrocarbon gas separated as the overhead fraction contains C3-C4 hydrocarbons and used as a recycle gas.

(e) Step of Mixing Feedstock Aliphatic Hydrocarbon and Recycle Gas

This step is a step where the recycle gas containing methane and/or ethane produced through the hydrogen gas separation step and the low boiling point hydrocarbon gas separated in the aromatic hydrocarbon separation step are mixed with the feedstock aliphatic hydrocarbon. The mixing may be carried out in distribution pipes. The resulting mixture is introduced in the above-described conversion reaction step. The mix ratio of the recycle gas and low boiling point hydrocarbon gas per the feedstock aliphatic hydrocarbon is from 0.1 to 10 part by weight, preferably from 0.5 to 3 part by weight. The use of methane and/or ethane as the recycle gas gives the following advantageous effects. That is, since the aromatization reaction by dehydrogenation cyclization is an endothermal reaction, the catalyst layer temperature is decreased, resulting in a disadvantage for aromatization. Methane and/or ethane are hardly aromatized under these conditions and thus can be deemed an inert gas. When methane and/or ethane have heat, they function as a heat supplying medium and can suppress the temperature in the catalyst layer from decreasing and can proceed with the reaction favorably. As the result, the aromatic hydrocarbon yield can be increased. Further, the recycling can decrease the partial pressure of hydrogen generated in the conversion reaction of the feedstock and thus can proceed with the aromatization reaction favorably. As the result, the aromatic hydrocarbon yield can be increased. Moreover, since the gas velocity in the reaction layer is increased (GHSV is increased), the contact time of the reactants and the catalyst active sites are shortened, and thus an excessive reaction providing coke-like substances can be suppressed. As the result, a reduction in activity occurring as the lapse of the reaction can be inhibited thereby retaining the aromatic hydrocarbon yield at a higher level. In a commercial device, the recycle gas ratio should be determined in economical view.

FIG. 1 shows a flow chart illustrating exemplarily the operation of the process of the present invention.

A mixture 6 of a feedstock aliphatic hydrocarbon and a light hydrocarbon gas which is a recycle gas is charged in reaction layers of the number of n (n is an integer of 2 or greater), containing the catalyst composition and arranged in series in a conversion reaction step 1 to be converted to an aromatic hydrocarbon, and then separated into a liquid component (high pressure separated liquid 8) containing mainly an aromatic hydrocarbon and a light gas (high pressure separated gas 9) in a gas-liquid separation step 2. The high pressure separated liquid 8 is supplied to a step of separating the aromatic hydrocarbon to remove a low boiling point hydrocarbon gas 13 thereby recovering an aromatic hydrocarbon 14.

Figure 2:
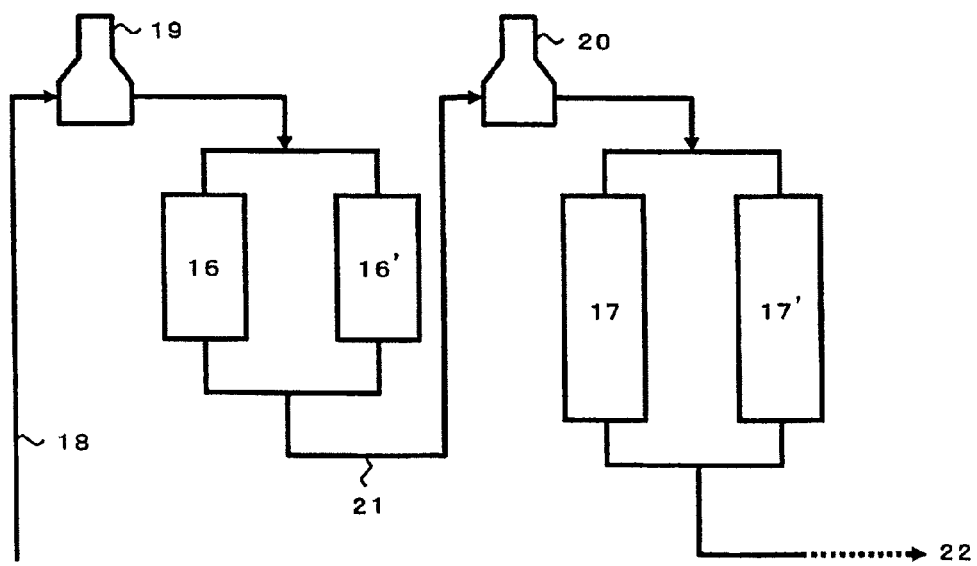
FIG. 2 shows one example of the conversion reaction step in the process of the present invention.

FIG. 2 shows one example of the conversion reaction step 1.

In the example shown in FIG. 2, the first stage reactor 16 and second stage reactor 17 are arranged in series, and a mixture 18 of a feedstock aliphatic hydrocarbon and a light hydrocarbon gas which is a recycle gas (corresponding to the mixture 6 in FIG. 1) is heated with a heating means 19 such as a heating furnace and introduced into the first stage reactor 16 to be converted. The first stage reactor 16 is provided with a catalyst in an amount of 30 percent by volume or less of the total catalyst amount and/or adjusted so that the aromatic yield in the effluent from the reactor 16 is from 0.5 to 30 percent by mass. The effluent 21 from the first stage reactor is heated again with a heating means 20 and then introduced into the second stage reactor 17 to be subjected to a conversion reaction again. The effluent 22 from the second stage reactor 17 may be heated again with a heating means such as a heating furnace and introduced into a third stage reactor, or alternatively may be introduced as the final effluent into the gas-liquid separation step 2 shown in FIG. 1. The reactor 16 and reactor 17 may be provided with another reactor 16' and another reactor 17', respectively so as to enable a continuous operation by carrying out the reaction and regeneration of the catalyst by removing coke depositing thereon by burning alternately in the reactors in the two lines.

APPLICABILITY IN THE INDUSTRY

The process of the present invention can produce aromatic hydrocarbons from a light hydrocarbon containing mainly hydrocarbons having 2 to 7 carbon atoms at a higher yield, than the conventional processes.

EXAMPLES

Hereinafter, the present invention will be described in more details by way of the following examples and comparative examples, which should not be construed as limiting the scope of the invention.

Reference Example 1

Production of Crystalline Aluminogallosilicate

Solutions (A) and (B) were prepared. Solution (A) contains 1,706.1 g of sodium silicate [J sodium silicate No. 3, $SiO_2$: 28 to 30 percent by mass, Na: 9 to 10 percent by mass, balance: water, manufactured by Nippon Chemical Industrial Co., Ltd.] and 2,227.5 g of water. Solution (B) contains 64.2 g of $Al_2(SO_4)_3 \cdot 14\text{-}18H_2O$ [Reagent special grade, manufactured by Wako Pure Chemical Industries, Ltd.], 32.8 g of $Ga(NO_3)_3 \cdot nH_2O$ [Ga: 18.51 percent, manufactured by Soekawa Chemical Co., Ltd.], 369.2 g of tetrapropylammonium bromide, 152.1 g of $H_2SO_4$ (97 percent by mass), 26.6 g of NaCl and 2,975 g of water. Thereafter, solution (B) was gradually added to solution (A) at room temperature while stirring. The resulting mixture was vigorously stirred in a mixer for 15 minutes to crush the gel thereby producing a homogeneous fine emulsion. Thereafter, the mixture was put in a stainless steel autoclave and crystallized under conditions where the temperature was 165° C., the time was 72 hours, the stirring rate was 100 rpm, and the pressure was self-pressure. After completion of the crystallization, the resulting product was filtered to recover the solid product. The solid product was washed and filtered repeatedly 5 times using about 5 liters of water. The resulting filtered solid product was dried at a temperature of 120° C. and calcined at a temperature of 650° C. under air circulation for 3 hours.

As the result of X-ray diffraction analysis, it was confirmed that the resulting calcined product had an MFI structure. The $SiO_2/Al_2O_3$ (molar ratio), $SiO_2/Ga_2O_3$ (molar ratio), and $SiO_2/(Al_2O_3+Ga_2O_3)$ (molar ratio) determined by MAS-NMR analysis were 64.8, 193.2, and 48.6, respectively. The amounts of the aluminum element and gallium element contained in the skeleton structure calculated from these results were 1.32 percent by mass and 1.16 percent by mass, respectively.

Reference Example 2

Preparation of Catalyst

Alumina powder (Cataloid AP, manufactured by JGC Catalysts and Chemicals Ltd.) was added to the crystalline aluminogallosilicate produced in Reference Example 1 so that the weight ratio of the aluminogallosilicate:alumina powder is 65:35, followed by addition of water. After the mixture was kneaded sufficiently, it was extruded and then dried at a temperature of 120° C. for 3 hours and calcined at a temperature of 600° C. under an air atmosphere for 3 hours. An about 2 normal ammonium nitrate aqueous solution was added to the extruded product at a rate of 5 ml per gram of the extruded product, followed by ion-exchange at a temperature of 100° C. for 2 hours. After this procedure was repeated 4 times, the product was dried at a temperature of 120° C. for 3 hours thereby producing an ammonium-type crystalline aluminogallosilicate shaped product. The product was made to have a size of 16 to 28 mesh and then calcined at a temperature of 600° C. under an air atmosphere for 3 hours thereby producing a hydrogen-type crystalline aluminogallosilicate catalyst.

Comparative Example 1

Using a flow type reaction unit for light naphtha conversion reaction, conversion reaction of light naphtha was carried out by packing 3 ml of the hydrogen-type crystalline aluminogallosilicate catalyst of Reference Example 2 into one of the reactors. The reactor was heated with an electric furnace arranged around the reactor. The experiment was carried out at a temperature at the entrance of the reactor of 550° C., a pressure at the exit of the reactor of 294 kPa (3.0 kgf/cm$^2$) and an LHSV of 0.8 hr$^{-1}$ by introducing nitrogen in an amount of 0.7 time by weight of the feedstock naphtha, as a gas simulating a recycle gas. The conversion products were analyzed by a gas chromatograph directly connected to the unit. The reaction results are set forth in Table 1 below. The reaction was carried out for 24 hours, and the aromatic yields set forth in table 1 were calculated form the analyzed values after the lapse of 24 hours from the initiation of the reaction. The light naphtha used in this example had the following characteristics: the initial boiling point of 36° C., end point of 91° C., specific gravity of 0.658 and sulfur content of 1 ppm by mass.

Comparative Examples 2 and 3

The hydrogen-type crystalline aluminogallosilicate catalyst of Reference Example 2 was used in an amount of 3 ml and packed in an amount of 50 percent by volume (1.5 ml)

thereof into each of a first reactor and a second reactor. Using a reaction unit where these reactors are arranged in series, a conversion reaction was carried out by heating the reactors with electric furnaces using the same naphtha as that of Comparative Example 1 as the feedstock. The reaction was carried out under the same conditions as those of Comparative Example 1 except that the temperature at the entrance of both of the reactors was 550° C. in Comparative Example 2, and the temperatures at the entrances of the first stage reactor and second stage reactor were 600° C. and 500° C., respectively in Comparative Example 3, the pressure at the exit of the second stage reactor was 294 kPa (3.0 kgf/cm²) both in Comparative Examples 2 and 3, for 24 hours. The composition of each of the products outflowing from the first stage reaction layer and conversion step exit was analyzed with a gas chromatograph directly connected to the reaction unit. Table 1 also sets forth the aromatic yields in the effluent from the first stage reaction layer and the overall conversion step, calculated from the analysis results after 24 hours.

Example 1

The hydrogen-type crystalline aluminogallosilicate catalyst of Reference Example 2 was used in an amount of 3 ml and packed in an amount of 50 percent by volume (1.5 ml) thereof into each of a first reactor and a second reactor. Using a reaction unit where these reactors are arranged in series, a conversion reaction was carried out at a temperature at the entrance of the first stage reactor of 550° C., a temperature at the entrance of the second stage reactor of 600° C., a pressure at the exit of the final stage reactor of 294 kPa (3.0 kgf/cm²) and an LHSV of 0.8 hr$^{-1}$ by introducing nitrogen in an amount of 0.7 time by weight of the feedstock naphtha, as a gas simulating a recycle gas. The reaction results are set forth in Table 1 below. The reaction was carried out for 24 hours, and the effluent was analyzed in the same manner as Comparative Example 2. The results are set forth in Table 1.

Examples 2 to 8

In each of Examples 2 to 8, using the same reaction unit as that used in the comparative examples, a conversion reaction was carried out by packing the hydrogen-type crystalline aluminogallosilicate catalyst of Reference Example 2 (total catalyst volume of 3 ml) into each of the reactors at each of the packing rates set forth in Table 1. The reactors were arranged in series and electric furnaces for heating were arranged therearound. The same light naphtha as that used in Comparative Example 1 was used as the feedstock. The reaction was carried out at a temperature at the entrance of each of the reactors of 550° C., a pressure at the exit of the final stage reactor of 294 kPa (3.0 kgf/cm²) and an LHSV of 0.8 hr$^{-1}$ by introducing nitrogen in an amount of 0.7 time by weight of the feedstock naphtha, as a gas simulating a recycle gas. The reaction results are set forth in Table 1 below. The reaction was carried out for 24 hours, and the effluent was analyzed in the same manner as Comparative Example 2. The results are set forth in Table 1.

As illustrated in the comparative examples and examples, it is apparent that the aromatic hydrocarbon can be produced in the effluent from the whole conversion reaction step at a high yield through a process of producing aromatic hydrocarbons by bringing a light hydrocarbon containing mainly paraffin and/or olefin having 2 to 7 carbon atoms into contact with a catalyst composition containing at least a gallium-containing crystalline aluminosilicate, wherein in a conversion reaction step where reaction layers the number of which is indicated by n are arranged in series and heating means are arranged between the reaction layers, the amount of the catalyst to be packed into the first reaction layer is adjusted to 30 percent by volume or less of the total catalyst amount and/or the aromatic yield of the effluent from the first stage reaction layer is adjusted to 0.5 to 30 percent by mass.

TABLE 1

| | Ratio of catalyst packed in each reaction layer (mass %) | | | | Aromatic yield in effluent from first stage reaction layer (mass %) | Aromatic yield in effluent from conversion reaction step (mass %) |
|---|---|---|---|---|---|---|
| | First stage reaction layer | Second stage reaction layer | Third stage reaction layer | Fourth stage reaction layer | | |
| Comparative Example 1 | 100 | — | — | — | — | 42.3 |
| Comparative Example 2 | 50 | 50 | — | — | 36.0 | 48.9 |
| Comparative Example 3 | 50 | 50 | — | — | 37.2 | 48.1 |
| Example 1 | 50 | 50 | — | — | 28.9 | 49.5 |
| Example 2 | 30 | 70 | — | — | 30.0 | 50.2 |
| Example 3 | 10 | 90 | — | — | 18.9 | 53.2 |
| Example 4 | 30 | 30 | 40 | — | 30.0 | 53.7 |
| Example 5 | 20 | 35 | 45 | — | 25.9 | 57.6 |
| Example 6 | 15 | 35 | 50 | — | 22.1 | 59.8 |
| Example 7 | 5 | 40 | 55 | — | 12.5 | 60.6 |
| Example 8 | 5 | 25 | 30 | 40 | 12.5 | 62.5 |

The invention claimed is:

1. A process for producing aromatic hydrocarbons, comprising bringing a feedstock containing mainly a light hydrocarbon having 2 to 7 carbon atoms into contact with a catalyst composition comprising at least a gallium-containing crystalline aluminosilicate, wherein a reaction step for converting the feedstock to aromatic hydrocarbons comprises at least two or more reaction layers formed of the catalyst composition, arranged in series and heating means arranged either between or in the reaction layers, and the amount of the catalyst in a first stage reaction layer is 30 percent by volume or less of the total catalyst volume.

2. The process according to claim 1, wherein when the number of the reaction layers in series is represented by n (n is an integer of 2 or greater), the catalyst amount in the first stage reaction layer is 60/n percent by volume or less of the total catalyst amount.

3. The process according to claim 1, wherein the gallium-containing crystalline aluminosilicate is a crystalline aluminogallosilicate.

4. The process according to claim 1, wherein the gallium-containing crystalline aluminosilicate is a crystalline aluminogallosilicate containing 80 percent by mass or more of particles having a diameter of 0.05 to 20 μm and containing 0.1 to 2.5 percent by mass of an aluminum element and 0.1 to 5.0 percent by mass of a gallium element.

5. The process according to claim 1, wherein a light gas containing mainly methane and/or ethane recovered from the effluent from the conversion reaction step is circulated thereto.

6. A process for producing aromatic hydrocarbons comprising bringing a feedstock containing mainly light hydrocarbons having 2 to 7 carbon atoms into contact with a catalyst composition comprising at least a gallium-containing crystalline aluminosilicate wherein a reaction step for converting the feedstock to aromatic hydrocarbons comprises at least two or more reaction layers formed of the catalyst composition, arranged in series and heating means arranged either between or in the reaction layers, the amount of the catalyst in a first stage reaction layer is 30 percent by volume or less of the total catalyst volume, and the yield of the aromatics in the effluent from the first reaction layer is from 0.5 to 30 percent by mass.

7. The process according to claim 6, wherein when the number of the reaction layers in series is represented by n (n is an integer of 2 or greater), the catalyst amount in the first stage reaction layer is 60/n percent by volume or less of the total catalyst amount.

8. The process according to claim 6, wherein the gallium-containing crystalline aluminosilicate is a crystalline aluminogallosilicate.

9. The process according to claim 6, wherein the gallium-containing crystalline aluminosilicate is a crystalline aluminogallosilicate containing 80 percent by mass or more of particles having a diameter of 0.05 to 20 μm and containing 0.1 to 2.5 percent by mass of an aluminum element and 0.1 to 5.0 percent by mass of a gallium element.

10. The process according to claim 6, wherein a light gas containing mainly methane and/or ethane recovered from the effluent from the conversion reaction step is circulated thereto.

* * * * *